US009029148B2

(12) United States Patent
Mayer

(10) Patent No.: US 9,029,148 B2
(45) Date of Patent: May 12, 2015

(54) METHODS FOR THE PREPARATION OF FIBROBLASTS

(75) Inventor: Barbara Mayer, Memmingen (DE)

(73) Assignee: Sphero Tec GmbH, Martineried (DE)

( * ) Notice: Subject to any disclaimer, the term of this patent is extended or adjusted under 35 U.S.C. 154(b) by 0 days.

(21) Appl. No.: 12/643,149

(22) Filed: Dec. 21, 2009

(65) Prior Publication Data
US 2010/0190252 A1 Jul. 29, 2010

(30) Foreign Application Priority Data

Dec. 22, 2008 (EP) .................................. 08022303

(51) Int. Cl.
C12N 15/85 (2006.01)
A01N 1/02 (2006.01)
C12N 5/077 (2010.01)

(52) U.S. Cl.
CPC .......... *C12N 5/0656* (2013.01); *C12N 2502/30* (2013.01); *C12N 2533/54* (2013.01); *C12N 2502/16* (2013.01)

(58) Field of Classification Search
None
See application file for complete search history.

(56) References Cited

U.S. PATENT DOCUMENTS

| | | | |
|---|---|---|---|
| 5,153,131 A | 10/1992 | Wolf et al. | |
| 5,153,132 A | 10/1992 | Goodwin et al. | |
| 5,153,133 A | 10/1992 | Schwarz et al. | |
| 5,155,034 A | 10/1992 | Wolf et al. | |
| 5,155,035 A | 10/1992 | Schwarz et al. | |

FOREIGN PATENT DOCUMENTS

WO WO/2005/010810 1/2005

OTHER PUBLICATIONS

Rogler et al (Scand. J. Gastroenterol. 2001. vol. 4, pp. 389-398).*
Merraim-Webster online dictionary: nest. 2011.*
Kunz-Schughart L. A. et al., A Heterologous 3-D Coculture Model of Breast Tumor Cells and Fibroblasts to Study Tumor-Associated Fibroblast Differentiation; Experimental Cell Research, May 15, 2001, vol. 266, No. 1, pp. 74-86, Academic Press; 2001.
Yuhas, J. M. et al., A Simplified Method for Production and Growth of Multicellular Tumor Spheroids, Cancer Research, Oct. 1977; vol. 37, pp. 3639-3643; University of New Mexico, Albuquerque New Mexico 87131.
Mueller-Klieser, Wolfgang, Multicellular Spheroids: A Review on Cellular Aggregates in Cancer Research; Cancer Research Clinical Oncology; 1987; vol. 113; pp. 101-122; Springer-Verlag 1987.
Hewitson et al., J Lab Clin Med, 140(3):199-208 (2002).
Kam et al., BMC Research Notes 2:130 (2009).
Moreno et al., Endocr. Pathol., 22:35-39 (2011).
Vollenweider and Hedinger, Virchows Archiv A, Pathol. Anat. Histopathol, 412:357-363 (1988).
PowerPoint slide published by Oxford University Press on behalf of the European Society of Human Reproduction and Embryology, 2006, Barnett K et al., Hum. Reprod. Update 2006; 12:537-555.
Definition of "Cell Nest," MediLexicon International Ltd., 2004-2014.

* cited by examiner

Primary Examiner — Celine Qian
(74) Attorney, Agent, or Firm — RatnerPrestia

(57) ABSTRACT

The invention relates to a process for generating fibroblasts, more particularly, to the culturing of fibroblasts in large numbers and of the heterogenic type. The invention is also directed to the use of fibroblasts in the preparation of heterotypic spheroids and a process for the preparation of such heterotypic spheroids.

19 Claims, No Drawings

METHODS FOR THE PREPARATION OF FIBROBLASTS

CROSS REFERENCE TO RELATED APPLICATIONS

This is a U.S. application claiming priority benefit of European application number EP 08 022 303.5 (filed Dec. 22, 2008), the content of such application being incorporated herein by reference.

FIELD OF THE INVENTION

The invention relates to a process for generating fibroblasts, more particularly, to the culturing of fibroblasts in large numbers and of the heterogenic type. The invention is also directed to the use of fibroblasts in the preparation of heterotypic spheroids and a process for the preparation of such heterotypic spheroids.

BACKGROUND OF THE INVENTION

In studies of tumour development, various in-vitro models have been applied. Generally, cells are grown in two-dimensional monolayers on plastic plates covered with liquid media that supplies essential nutrients and growth factors for the cells.

Even though two-dimensional monolayer culture has provided great benefits to scientists and clinicians, this culture system suffers from a particular lingering disadvantage. This method of cell culture does not mimic effectively the in-vivo environment from which the cells were originally isolated. Cells, such as tumour cells, do not grow in two-dimensional monolayers within the body. Rather, the in vivo environment involves interactions between cells of different types in three dimensions. Thus, two-dimensional monolayer or two-dimensional suspension cell cultures cannot accurately reflect the true three-dimensional cellular architecture found in vivo.

Unsurprisingly, cells cultured in monolayers do not exhibit the same biological responses seen in vivo. In a monolayer, all of the cells have the same growth conditions which results in a homogenous cell population wherein every cell is like every other cell in the culture system. In contrast, naturally occurring cells generally represent a heterogeneous cell population resulting, for example, from positional cues, cell differentiation and differences in the multi-cellular and biochemical environment such as hormones, growth factors, oxygen tension, cytokines, chemokines etc.

To mimic the properties of the naturally occurring cellular environment more closely, three-dimensional cell culture systems have been developed for use in medical and biological research. Usually these systems utilise well established cell lines on the basis that their use allows standardisation and comparability of results between experiments. These three-dimensional cultures are essentially homotypic, meaning that they are made up of only one cell type. Thus, such cultures cannot reflect accurately the heterotypic in vivo environment.

Fibroblasts have key functional roles in the tissues in which they reside, synthesizing and maintaining the extracellular matrix of body tissue. Fibroblasts provide a structural framework (stroma) for many tissues, play a critical role in wound healing and are the most common cells of connective tissue in animals.

The main function of fibroblasts is to maintain the structural integrity of connective tissues by continuously secreting precursors of the extracellular matrix. Fibroblasts secrete the precursors of all the components of the extracellular matrix, primarily the ground substance and a variety of fibres. The composition of the extracellular matrix determines the physical properties of connective tissues.

Further, fibroblasts are capable of producing cytokines (such as e.g. interleukins, cgfbeta, IGF-1), chemokines (such as e.g. CXCL12), growth factors (such as e.g. hgf, vegf, fgf, egf), proteases (such as e.g. MMPs, CIMPs) and other soluble factors (such as e.g. S100A4).

Fibroblasts are morphologically heterogeneous with diverse appearances depending on their location and activity. Ectopically transplanted fibroblasts often retain positional memory of the location and tissue context where they had previously resided, even over several generations.

Unlike epithelial cells that line the bodies structures, fibroblasts do not form flat monolayers and are therefore not restricted by a polarising attachment to a basal lamina on one side. Fibroblasts can also migrate slowly over the substratum as individual cells. Whilst epithelial cells, for example, form the lining of body structures, fibroblasts and related connective tissues sculpt the "bulk" of an organism.

As a result of these interactions with other cells, fibroblasts have been found to play a role in tumour formation. As tumour fibroblasts or myo-fibroblasts, they are believed to be important in both tumour development and tumour progression.

For these reasons, heterotypic spheroids have been developed as three dimensional tumour models wherein standardised cell lines are combined with fibroblasts. These methods require large amounts of fibroblast cells. Unfortunately, fibroblasts can so far only be grown in the laboratory in small quantities.

Further, to generate spheroids closely resembling the natural tumour and/or tissue characteristics, the fibroblasts used have to be of a heterogenic type.

Thus, there is a need in the art for methods of producing large amounts of fibroblasts, particularly from limited amounts of starting material which are of heterogenic type.

SUMMARY OF THE INVENTION

The invention therefore provides a process for the preparation of fibroblasts comprising the steps of:
a) Providing a cell-containing tissue sample;
b) Preparing a suspension of primary cells;
c) Culturing the suspension of primary cells wherein fibroblast cell nests are generated from and within the suspension of primary cells;
d) Separating the fibroblast cell nests of step (c) from the suspension of primary cells;
e) Repeating steps (c) to (d) at least once.

The present invention is further directed to fibroblasts obtained by this process.

The term "heterogenic fibroblasts" is thereby to be understood as encompassing fibroblasts of a different phenotype and genotype.

In addition, the invention is directed to a process for the preparation of heterotypic multi-cellular spheroids and to a multicellular spheroid obtained by the process.

Finally, the present invention is directed to the use of the fibroblasts of the invention for the generation of spheroids.

DETAILED DESCRIPTION OF THE PREFERRED EMBODIMENTS

Throughout this application various articles and patents are identified. The disclosures of these documents are hereby incorporated in their entirety by reference into this application.

The preparation of the suspension of primary cells according to step b) of the process of the invention can be carried out by a mechanical treatment such as crushing with a scalpel or lancet, but may be also carried out by dissolving or dissipating the tissue in a suitable solvent such as for example a culture medium as defined above and/or an enzyme preparation and/or buffer by—for example—stirring or another suitable method. In a preferred embodiment of the process of the present invention, the suspension of primary cells of step b) is also treated with an enzymatic composition containing one or more enzymes selected from the group consisting of proteases such as serin proteases such as trypsin or dispases, neutral proteases; metalloendopeptidases such as collagenases such as interstitial collagenases and neutrophil collagenases or thermolysin; DNases; hyaloronidases; before culturing according to step c).

In a particularly preferred embodiment, the enzymatic composition also contains a serum-free medium selected from the group consisting of RPMI, DMEM, F15, MEM, BMEEARL, HAMFSF-12, Leibovitz L-15, McCoys 5A, medium 199, Waymouth medium and HANK-solution. Further preferred, the enzymatic composition is serum-free.

In a further particularly preferred embodiment, the enzymatic composition contains glucose in an amount of equal to or less than 1 g/l.

The additional (and optional) treatment with an enzymatic composition as outlined before has the advantage that the cells of the suspension of primary cells possess a further increased vitality compared to the primary cells of suspensions which are only subjected to a mechanical and/or dissipation treatment. Further, a higher yield of primary cells can be obtained when also treated with an enzymatic composition.

In a particularly preferred embodiment, the treatment with the enzymatic composition is carried out in a water bath, preferably a shaking water bath, at a temperature of 35-39° C., preferably 37° C., and for a time range of from 1 minute to several hours, preferably 5 minutes to 2 hours and most preferred from 15 minutes to 45 minutes.

An enzymatic composition which is particularly preferred comprises 2.5 mg/ml collagenase 1 or 2 mg/ml collagenase A, 1 mg/ml hyaloronidase, 0.2 mg/ml DNase, 1 mg/ml dispase, 0.1 mg/ml trypsin, 1.8 mg/ml protease and 0.28 mg/ml thermolysin. In a further particularly preferred embodiment the enzymatic composition also comprises a medium selected from DMEM and MEM and does not encompass a serum.

As used herein, the term "homotypic" refers to cells of a single type. For example, commercially available cell lines are generally homotypic. In contrast and as used herein, the term "heterotypic" refers to cells of more than one cell type. For example, primary isolate tissue comprising different cell types will be heterotypic.

Preferably the cell-containing tissue is a primary isolate tissue sample. In the methods of the present invention, preferably the cell containing tissue for generating the fibroblasts comprises somatic cells, stem cells, cancer cells, progenitor cells and/or cancer stem cells.

In the sense of the present invention, the term "somatic cell" comprises any cell from a multi-cellular organism that composes the body of that organism and that is not a sperm or egg cell. Preferably the tissue originates from a mammal.

As used herein, the term "primary isolate tissue sample" refers to biological tissue and/or cell containing bodily fluid(s) that has/have been obtained directly from, for example, an individual, patient or animal without intermediate steps of subculture through a series of cultures and/or hosts. Thus, in the method of the invention, a suspension of primary cells is produced directly from the primary isolate tissue sample. This is in contrast to established cell lines used in the prior art and which are far removed from being directly derived from their progenitor tissue by several, often a great many, intermediate culture steps. By way of non-limiting example, sources of suitable tissues include benign or malignant primary and metastatic tissues. Sources of suitable cell containing bodily fluids include pleural effusion fluid or ascites fluid (liquid tumours). The tissue used may be a normal or healthy biological tissue, or may be a biological tissue afflicted with a disease or illness such as a tumour tissue.

Primary tumours are tumours from the original location in the body where they first developed. For example, a primary brain tumour is one that aroses in the brain. This is in contrast to metastatic tumours that arise elsewhere and metastasise or spread to other locations in the body, for example, the brain.

The tissue may be a normal or healthy biological tissue or may be a biological tissue afflicted with a disease or illness such as a tissue or fluid derived from a tumour or an inflammatory tissue. The tissue may be obtained from a human, for example, from a patient during clinical surgery or from a biopsy. Alternatively the tissue may be obtained from an animal such as from mouse, rat, rabbit and the like.

According to a preferred embodiment of the process according to the invention the cell containing tissue sample is either benign tissue such as gastric tissue, colorectal tissue, liver tissue, lung tissue, mucosal tissue, cerebral tissue, pancreas tissue, hepatic tissue, dermal tissue, prostate or periprostatic tissue, gastric tissue, colonic tissue, ovarial tissue, breast tissue, cervical tissue or glioma tissue or malign tissue such as tumour tissue such as tumour tissue from gastric, pancreas, colorectal, liver, lung, breast, cervical, mucosal, cerebral, hepatic dermal, colonic, ovarial, sarcoma, prostate or glioma tumours.

Particularly preferred tumour tissue is gastric, pancreas, colorectal, liver, lung, breast, cervical, sarcoma, prostate or glioma tumour tissue. Also encompassed by the invention is a tissue, which comprises metastatic cells, progenitor cells or cancer stem cells. Tissue arising from and comprising other cell types is also within the scope of the invention such as smooth muscle cells, adipocytes, neural cells, stem cells, islet cells, foam cells, hepatocytes and bone marrow cells.

When the tissue is a mucosa tissue this may include alveolar mucosa, gland mucosa, gastric mucosa, intestinal mucosa, nasal mucosa, stomach mucosa or ectopic gastric mucosa.

Preferably the tissue is directly derived from the tissue of a patient or healthy donor, a tissue derived from surgery such as surgical specimens, a biopsy and also cells from cell-containing body fluids such as aspiration, ascetics, pleural effusion or drainage.

In the process according to the invention the cell containing tissue sample is first treated mechanically to dissociate or separate the cells of the tissue from each other. The term "mechanically" means that the tissue is treated to disrupt the connections between associated cells, for example, using a scalpel or scissors or by use of a machine, such as a homogenizer. The mechanical treatment of the tissue can, however, be accomplished by any means known to a person skilled in the art as suitable for the inventive purpose.

Preferably the cell containing tissue sample is reduced to small pieces by the use of a scalpel before suspending in a medium to produce a suspension of primary cells.

Preferably the medium is a growth medium. Further preferred, the cell containing tissue sample is suspended in a vessel coated with a matrix. As a matrix, any material known to a person skilled in the art as suitable for the inventive purpose can be used, for example, gelatine such as gelatine type A, Fibronectin, Vibronectin, Collagen or Laminin or a mixture of any of these.

The growth medium preferably comprises at least one component selected from a buffer, a serum, an antibiotic and a fungicide.

Preferably the buffer is a phosphate buffered saline (PBS), comprising sodium chloride, sodium phosphate and may comprise other components such as potassium chloride and potassium phosphate. Yet more preferably the buffer is isotonic. It is preferred that the PBS is free of $CaCl_2$ and $MgCl_2$.

Preferred serum includes foetal calf or bovine serum (FCS or FBS).

A preferred antibiotic is a cephalosporin such as Cefazoline, also known as Cefazoline or Cephazolin. Cefazolin is commonly used in the treatment of bacterial infections and is clinically effective against infection with staphylococci and streptococci species of gram positive bacteria. Thus, in the sense of the present invention, Cefazoline may be used to prevent bacterial infection of the tissue culture.

A preferred fungicide comprises Amphotericin B, an antifungal polyene antibiotic. Amphotericin B is designated chemically as [1R-(1R*, 3S*, 5R*, 6R*, 9R*, 11R*, 15S*, 16R*, 17R*, 18S*, 19E, 21E, 23E, 25E, 27E, 29E, 31E, 33R*, 35S*, 36R*, 7S*)]-33-[(3-Amino-3,6-dideoxy-β-D-mannopyranosyl)-oxy],3,5,6,9,11,17,37-octahydroxy-15,16,18-trimethyl 13-oxo-14,39-dioxabicyclo[33.3.1]nonatriaconta-19,21,23,25,27,29,31-heptaene-36-carboxylic acid. For example, fungizone comprises amphotericin B and sodium desoxycholate.

As stated above, the suspension of primary cells is then cultured. The culturing is preferably carried out by incubating the suspension in a vessel coated with a matrix which is preferably gelatine.

Suitable culturing times are from about 1 minute to several months, preferred from 1 hour to several weeks, more preferred from 24 hours to 10 weeks, also preferred from 2 days to 4 weeks, and most preferred from 3 days to 2 weeks, wherein 1 week is also preferred. The temperature is preferably from about 25° C. to 40° C., preferably from 35° C. to 39° C., more preferred from 36° C. to 38° C. and is most preferred 37° C. Most preferred the incubation time is 1 week at a temperature of 37° C.

During culturing, the tissue culture is checked for contamination, for example bacterial or fungal contamination. The tissue culture is preferably checked for contamination after 3 days of culturing but may be also checked for contamination after 2 or 4 days of culturing. If no contamination is detected, the suspension is further cultured. The culturing can then be carried out in the same fashion as before. The check for contamination may, however, also be carried out between different culturing conditions. It may further be advantageous during the culturing to remove the growth medium, or at least a part thereof, and replace it with fresh growth medium. By changing the culturing conditions during culturing a more specific adaption to optimal culturing conditions for the whole culturing process can be achieved.

After the first run of culturing the fibroblast nests which were generated on the matrix of the vessel and the suspension are separated.

The separation can be carried out by any means known to a person skilled in the art as suitable for the inventive purpose. Preferably, the separation is carried out by taking up the suspension with a pipette.

The tissue that is adhered to the surface of the vessel (that is, the tissue consisting of the fibroblast nests generated) can then be detached by mechanical or enzymatical means. Further, the cell nests can be harvested by treating with, for example, a mixture of Trypsin/EDTA. As a result of such treatment, the cell nests may be detached from the surface. Other methods of detaching cells are known to the person skilled in the art.

After harvesting the cells, the detaching solution is removed. This may be done by centrifugation, thereby obtaining a fibroblast cell pellets and a supernatant that can be easily removed. The resulting fibroblast cell pellets may then be re-suspended in a freezing medium and stored cold, for example, at a temperature of from −200° C. to −20° C., preferably of from −196° C. to −40° C., more preferred of from −190° C. to −80° C. and most preferred at −180° C. Storage is preferably effected in liquid nitrogen.

In contrast to the methods of the prior art, the suspension is not discarded at this stage but is transferred to a second vessel as described above and fresh culture medium is added. Preferably the second vessel is also coated with gelatine solution. Before the suspension is transferred to a second vessel, the suspension is preferably centrifugated to separate the cells and biopsy-like cell clusters from the suspension. In this case, only the cells and biopsy-like cell clusters are transferred to a second vessel.

Surprisingly it has been discovered that fibroblasts can continue to be generated/extracted from the tissue suspension by repeating the culturing step in this manner. This allows it to generate fibroblasts in far greater quantities from a limited starting material with fewer culture passages than has been possible before.

The culturing step may be repeated at least 2 times, preferably 3 to 12 times, more preferred 3 times to 10 times and most preferred 4 times to 8 times thereby generating several batches of fibroblasts.

According to the method of the present invention, the fibroblasts generated from each step of culturing are heterogenic which means: of different phenotypes and genotypes. This is due to the fact that within each batch a different type of fibroblast cell is prepared to adhere to the matrix of the vessel and to proliferate. After carrying out several steps of culturing, the method developed by the inventors of the present invention allows it therefore to generate fibroblasts with a heterogenic structure. Within the state of the art, only fibroblasts of a homogenic type could have been generated.

The above described process results in a number of batches of fibroblasts. Surprisingly it has been found that the cells of each batch are of a different type. This is advantageous for the preparation of heterotypic spheroids.

The invention is also directed to the use of fibroblasts obtained by to the process of the present invention as described before for the preparation of multi-cellular spheroids. The spheroids are preferably heterotypic and comprise the fibroblasts generated according to the invention.

Moreover, the invention also relates to a process for the preparation of multi-cellular spheroids comprising:
a) Preparing a suspension of single cells from at least one biological tissue or cell-containing bodily fluid;
b) Adding fibroblasts obtained by the process of the present invention;
c) Adjusting the concentration of cells in the suspension to a concentration in the range of from $10^3$ cells to $10^7$ cells;
d) Adding 2 vol.-% to 50 vol.-% of an inert matrix to the suspension of single cells; and
e) Incubating the suspension of single cells.

As used herein, the term "three dimensional cell culture" refers to any method usable to effect the growth of cells in a three dimensional multi-cellular form such as spheroids.

As used herein, the term "spheroid" refers to an aggregate, cluster or assembly of cells cultured to allow three-dimensional growth in contrast to the two-dimensional growth of cells in either a monolayer or cell suspension (cultured under conditions wherein the potential for cells to aggregate is limited). The aggregate may be highly organized with a well defined morphology or it may be a mass of cells that have clustered or adhered together with little organisation reflecting the tissue of origin. It may comprise a single cell type (homotypic) or more than one cell type (heterotypic). Preferably the cells are primary isolates but may also include a combination of primary isolates with an established cell line(s). Particular cell "types" include somatic cells, stem cells, cancer cells, progenitor cells and cancer stem cells.

Spheroids may comprise a single cell type (homotypic spheriods) or more than one cell type (heterotypic spheriods). In the sense of the present invention, the heterotypic spheroids are to be understood as a combination of fibroblasts produced according to the present invention with cells of either primary isolates or established cell line(s), for example. Particular cell types include somatic cells, stem cells, cancer cells, progenitor cells and cancer stem cells.

The process for the preparation of heterotypic multi-cellular spheroids preferably comprises: preparing a suspension of single cells from a cell line or primary isolate tissue sample, adjusting the concentration of cells in the suspension to an appropriate concentration, adding an appropriate amount of a thickening agent to the suspension of single cells and combining and incubating the suspension of single cells with fibroblasts obtained according to the present invention, preferably in the presence of $CO_2$. The concentration of $CO_2$ is thereby preferably from 1 vol.-% to 10 vol.-%, preferred from 2 vol.-% to 8 vol.-%, more preferred from 4 vol.-% to 6 vol.-% and most preferred 5 vol.-%.

In a preferred embodiment of the present invention, the single cell suspension is prepared in a medium comprising serum, buffer, interleukins, chemokines, growth factors, hydrogen carbonate, glucose, physiological salts, amino acids and/or hormones.

In a particularly preferred embodiment of the present invention, the tissue is preferably treated mechanically and/or enzymatically before preparing the suspension of single cells.

The term "mechanically" is therefore to be understood as defined before. The term "enzymatically" is to be understood as to treat the tissue using one or more enzymes such as for example collagenase, dispases, DNAse and/or hyaluronidase. Preferably a cocktail of enzymes is used under different reaction conditions, such as for example incubation at 37° C. in a water bath or at room temperature while shaking.

The tissue used is preferably selected from healthy tissue, inflammatory tissue, tumour tissue, benign or malignant primary and metastatic tissue. Preferably the tissue is a mammalian tissue. The suspension of single cells as described above may however also be prepared starting from cells originating from one or more cell containing bodily fluids. Further, the single cells suspension may be prepared based on cells originating from one or more tissue(s) and one or more cell containing bodily fluids.

In particular embodiments of the present invention, the single cell suspension is directly derived from a primary isolate tissue.

As used herein, the term "directly derived" refers to a suspension of single cells from a biological tissue and/or cell containing bodily fluid that has been obtained directly from an individual, donor patient or animal without intermediate steps of subculture through a series of cultures and/or hosts. Thus, a suspension of single cells is produced directly from the biological tissue and/or cell-containing bodily fluid. This is in contrast to established methods in which stable and highly passaged cell lines are used. Such cell lines are far removed from being directly derived from their progenitor tissue by several intermediate culture steps. Sources of suitable tissues include for example benign or malignant primary and metastatic tissues, sources of suitable cell containing bodily fluids include for example pleural effusion fluid or ascites fluid (liquid tumors).

A "primary culture" is an initial culture of cells freshly isolated from a tissue.

The term "cell line" as used herein refers to cells derived from a primary culture by subculturing and that have exceeded the Hayflick limit. The Hayflick limit may be defined as the number of cell divisions that occur before a cell line becomes senescent or unable to replicate further. This limit is approximately 50 divisions for most non-immortalized cells and in terms of cell culture, equates to approximately 9 to 10 passages of cell subculture over the course of from about 12 to 14 weeks.

Primary tumors are tumors from the original site where they first developed. For example, a primary brain tumor is one that aroses in the brain. This is in contrast to a metastatic tumor that arises elsewhere and metastasized or spread to, for example, the brain.

According to the invention the tissue which may be used for spheroid preparation may be a normal or healthy biological tissue, or may be a biological tissue afflicted with a disease or illness, such as a tissue or fluid derived from a tumor. Preferably the tissue is a mammalian tissue. Also encompassed are metastatic cells. The tissue may be obtained from a human, for example from a patient during a clinical surgery or from biopsies. The tissue may also be obtained from animals such as mice, rats, rabbits, and the like. It is also possible according to the invention to prepare spheroids from stem cells, progenitor cells or cancer stem cells.

Besides cells originating from tumor tissue, other cells with various indications such as smooth muscle cells, adipocytes, neural cells, stem cells, islet cells, foam cells, fibroblasts, hepatocytes and bone marrow cells, cardiomyocytes and enterocytes are also encompassed within the present invention.

Also within the scope of the present invention is the possibility to rebuild a metastatic microtumor e.g. tumor cells with hepatocytes, or tumor cells with bone marrow cells.

Also useful within the invention are primary cancer cells such as gastric, colon and breast primary cancer cells and metastatic cells. Also encompassed by the invention are primary normal (healthy) cells such as endothelial cells, fibroblasts, liver cells, and bone marrow cells.

Preferably the cells are directly derived from the tissue of a patient or healthy donor, a tissue derived from a biopsy, surgical specimens and also cells from cell-containing bodily fluids such as aspiration, ascetics, pleural effusion or drainage.

Also within the scope of the invention are large spheroids which consist of a higher cell number in the range of preferably from $10^6$ to $5 \times 10^6$ cells. Large spheroids generally have a necrotic/apoptotic centre that correlates with the upregulation of various biomarkers such as HIF-1alpha, VEGF, TKTL-1 and others. Large and small spheroids are generally used for different purposes, for example, large spheroids may be used as a model of advanced tumors.

The multicellular spheroids according to the invention can be used for diagnostic and/or therapeutic purposes, for example, pharmacokinetic profiling, pharmacodynamic profiling, efficacy studies, cytotoxicity studies, penetration studies of compounds, therapeutic resistance studies, antibody generation, personalized or tailored therapies, RNA/DNA "drug" testing, small molecule identification and/or testing, biomarker identification, tumour profiling, hyperthermia studies, radioresistance studies, anti-angiogenic studies co-culturing with endothelial cells and the like.

The concentration of cells in the suspension is adjusted in the range of from $10^3$ to $10^7$ cells/ml medium. 2 vol.-% to 50 vol.-% of an inert matrix is then added to the suspension of single cells, which is then incubated, preferably in the presence of $CO_2$ as defined before.

In the process according to the invention the cells of the biological tissue and/or cell containing bodily fluid are first dissociated or separated from each other. Dissociation of the tissue is accomplished by any conventional means known to those skilled in the art. Preferably the tissue is treated mechanically or enzymatically as defined before. More preferably the tissue is treated both mechanically and enzymatically.

The dissociated tissue is then suspended in a medium to produce a suspension of single cells. The suspension is then cultured as described to generate fibroblast cell nests. Afterwards the fibroblast cell nests are separated from the suspension. According to the present invention these steps of culturing the suspension and separation of the generated fibroblast nests are repeated at least once, gaining different types (phenotypic and genotypic) of fibroblasts within each step.

It should be noted that prior art methods generally include the two-dimensional tissue culture of fibroblasts which are homogenic (that means are of the same phenotype and genotype) prior to attempting three-dimensional cell cultivation.

In contrast thereto, it has surprisingly been found that spheroids produced from suspensions of single cells prepared from primary isolate tissue according to the present invention retain essentially all of the biological properties of the originating biological tissue. This is the case for both homotypic and heterotypic cell systems. The same applies when cell-containing bodily fluids are used.

Preferably the suspension of single cells is treated to remove dead and/or dying cells and/or cell debris. The removal of such dead and/or dying cells is accomplished by any conventional means known to those skilled in the art for example, using beads and/or antibody methods. It is known, for example, that phosphatidylserine is redistributed from the inner to the outer plasma membrane leaflet in apoptotic or dead cells. Annexin V and any of its conjugates which have a high affinity for phosphatidylserine can therefore be bound to these apoptotic or dead cells. The use of Annexin V-Biotin binding followed by binding of the biotin to streptavidin magnetic beads enables separation of apoptotic cells from living cells. Other suitable methods will be apparent to the skilled artisan.

Methods of the prior art often utilize a dye exclusion test to monitor the vitality or viability of cells. The dye exclusion test is used to determine the number of viable cells present in a cell suspension. It is based on the principle that livingcells possess intact cell membranes that exclude certain dyes, such as trypan blue, eosin, or propidium iodide, whereas dead cells do not. In the trypan blue test, a cell suspension is simply mixed with dye and then visually examined to determine whether cells take up or exclude dye. A viable cell will have a clear cytoplasm whereas a nonviable cell will have a blue cytoplasm. Dye exclusion is a simple and rapid technique measuring cell viability but it is subject to the problem that viability is being determined indirectly from cell membrane integrity. Thus, it is possible that a cell's viability may have been compromised (as measured by capacity to grow or function) even though its membrane integrity is (at least transiently) maintained.

Conversely, cell membrane integrity may be abnormal yet the cell may be able to repair itself and become fully viable. Another potential problem is that because dye uptake is assessed subjectively, small amounts of dye uptake indicative of cell injury may go unnoticed. In this regard, dye exclusion performed with a fluorescent dye using a fluorescence microscope may result in the scoring of more nonviable cells with dye uptake than tests performed with trypan blue using a transmission microscope. As a result of the use of this method, the suspensions of single cells and spheroids of the prior art comprise a far greater proportion of apoptotic or dead cells. This inclusion of dead matter means that the prior art spheroids are less able to mimic the conditions found in biological tissue in vivo.

A more sophisticated method of measuring cell viability is to determine the cell's light scatter characteristics, 7AAD or propidium iodide uptake. It will be apparent to one skilled in the art that the use of a flow cytometer coupled with cell sorting may also accomplish removal of dead and/or apoptotic cells.

The suspension of single cells is prepared in a culture medium. The medium is designed such that it is able to provide those components that are necessary for the survival of the cells. Preferably the suspension of single cells is prepared in a medium comprising one or more of the following components: serum, buffer, interleukins, chemokines, growth factors, hydrogen carbonate, glucose, physiological salts, amino acids and hormones.

A preferred medium is RPMI 1640. RPMI 1640 was developed by Moore et. al. at Roswell Park Memorial Institute (hence the acronym RPMI). The formulation is based on the RPMI-1630 series of media utilizing a bicarbonate buffering system and alterations in the amounts of amino acids and vitamins. RPMI 1640 medium has been used for the culture of human normal and neoplastic leukocytes. RPMI 1640, when properly supplemented, has demonstrated wide applicability for supporting growth of many types of cultured cells.

Preferably, the medium further comprises L-glutamine, in particular a stabilized L-glutamine. L-glutamine is an essential nutrient in cell cultures for energy production as well as protein and nucleic acid synthesis. However, L-glutamine in cell culture media may spontaneously degrade, forming ammonia as a by-product. Ammonia is toxic to cells and can affect protein glycosylation and cell viability, lowering protein production and changing glycosylation patterns. It is thus preferred that the L-glutamine is a stabilized glutamine, most preferably it is the dipeptide L-alanyl-L-glutamine, which prevents degradation and ammonia build-up even during long-term cultures. The dipeptide is commercially available as GlutamaxI®.

The medium may further comprise additional components such as antibiotics, for example, penicillin, streptomycin, neomycin, ampicillin, metronidazole, ciprofloxacin, gentamicin, Amphotericin B, Kanamycin, Nystatin; amino acids such as methionine or thymidine; FCS and the like.

In addition to, or instead of, RPMI1640 other liquid media can be used, for example DMEM high or low glucose, Ham's F-10, McCOY's 5A, F-15, RPMI high or low glucose, Medium 199 with Earle's Salts or the different variants of MEM Medium.

In a next step, the suspension of single cells is combined with fibroblasts produced according to the first aspect of the present invention.

The fibroblasts may be combined with the suspension of single cells at a ratio of from about 1:1, 2:1, 3:1, 4:1, 5:1, 6:1, 7:1, 8:1, 9:1, or greater, wherein a ratio of 2:1 would represent two fibroblast cells to every cell in the suspension of single cells. Alternatively, the ratio of fibroblasts to cells in the suspension of single cells may be reversed, i.e., 1:2, 1:3, 1:4, 1:5, 1:6, 1:7, 1:8, 1:9 or greater. It will be apparent to one skilled in the art that these ratios are approximate values based on, for example, calculated cell concentrations, since it would be impractical to count absolute numbers of cells.

The advantage of combining, for example, homotypic cell types with fibroblasts produced according to the first aspect of the invention is that tumour cells interact with fibroblasts (and also with other cell types) in nature. Hence, the combination with such cells leads to a heterotypic, multi-cellular spheroid system which mimics even more closely an in vivo cell or metastic cell system.

The internal environment of a spheroid is dictated by the metabolism and adaptive responses of cells with a well-defined morphological and physiological geometry. Most homotypic spheroids develop concentric layers of heterogeneous cell populations with cells at the periphery and layers of quiescent cells close to a necrotic core. The heterogeneous arrangement of cells in a spheroid mimics initial avascular stages of early tumours. Although homotypic spheroids are able to mimic closely the in vivo morphology, some of the biological complexity is lost. Accordingly, by combining more than one cell type, tumour cell interactions with other cell types reflecting natural cell interaction in vivo can be established better representing the in vivo environment.

Fibroblasts produced according to the invention may be further combined with other cells, for example from established cell lines, primary cells and/or primary or metastatic tissues. Most preferably the tissue is a tumour tissue wherein the cancer cell lines may be cell lines from gastric (e.g. Hs-746T, MKN-28, N87, and the like), colorectal (e.g. HT-29, HCT-116, DLD-1, and the like), liver (e.g. HepG2), pancreas (e.g. L.3.6pl, AsPC-1, MIAPACA, and the like), lung (e.g. A549, H358, H1299, and the like), kidney (e.g. 786-O, A-498, CAKI-1, and the like), breast (e.g. MCF-7, BT549, Hs575T, and the like), cervical (e.g. HeLa), prostate (e.g. PC-3, LNCaP, DU-145, and the like) or glioma (e.g. U251, U373, and the like) cell lines. It is, however, emphasized that the method according to the present invention is suitable for use with any cell line. In particular preferred are also cell lines from sarcoma or astrocytoma tissue.

In a next step of the method, the concentration of cells in the suspension is adjusted to an appropriate cell concentration. An appropriate cell concentration means an amount of cells per milliliter of culture medium which supports the formation of spheroids in the incubation step. Appropriate cell amounts are preferably $10^3$ to $10^7$ cells/ml medium, more preferably $10^3$ to $5 \times 10^6$ cells/ml medium and most preferred $10^5$ to $10^6$ cells/ml medium. Methods of determining cell concentration are known in the art, for example, the cells may be counted with a Neubauer counter chamber (hemocytometer).

In a next step of the process of the present invention an appropriate amount of an inert matrix is added to the suspension of single cells. Use of the term "inert" as used herein refers to a matrix that has limited or no ability to react chemically and/or biologically, i.e. having little or no effect on the biological behaviour or activity of the cells in the suspension. Ideally the inert matrix is of non-human origin.

Preferably the inert matrix increases the viscosity of the culture medium. Not wishing to be bound by theory, it is believed that increasing the viscosity of the culture fluid increases the co-incidental collision and adherence of cells with each other resulting in the formation of aggregates. This is particularly useful since it improves the ability of shear sensitive or weakly adherent cells to aggregate and develop into spheroids.

Thus, the inert matrix supports or promotes the formation of spheroids during the incubation step. Preferably the inert matrix is added to the culture medium in an amount of 2 vol.-% to 50 vol.-% based on the total volume of the medium. Preferably the inert matrix is added in an amount of 5 vol.-% to 30 vol.-%, most preferably in an amount of 20 vol.-% to 30 vol.-%. Particular amounts will vary depending on the source or composition of the cells such as 3 vol.-%, 4 vol.-% or 5 vol.-% up to 10 vol.-% or 15 vol.-% for cell lines and up to 30 vol.-% to 45 vol.-% or 50 vol.% when using primary isolate tissue. These amounts are based on the total volume of the medium. The inert matrix is preferably a non-ionic poly(ethylene oxide) polymer, water soluble resin or water soluble polymer such as a cellulose ether. Preferably the inert matrix is selected from the group comprising carboxymethyl cellulose, hydroxypropyl cellulose, hydroxypropylmethyl cellulose, hypomellose, methyl cellulose, methylethyl cellulose. However, also suitable is cellulose, agarose, seaplaque agarose, starch, tragacanth, guar gum, xanthan gum, polyethylene glycol, and the like.

In the next process step of the present invention the single cell suspension is incubated, preferably in the presence of $CO_2$. Incubation can also be carried out in the presence of water vapour. The concentration of $CO_2$ is thereby preferably from 1 vol.-% to 10 vol.-%, preferred from 2 vol.-% to 8 vol.-%, more preferred from 4 vol.-% to 6 vol.-% and most preferred 5 vol.-%. Possible preparation techniques are e.g. the liquid-overlay technique, the spinner flask technique, the high aspect rotating vessel (HARV) technique or the hanging drop method. These methods are known to the skilled artisan. The HARV technique is inter alia disclosed in U.S. Pat. Nos. 5,153,131, 5,153,132, 5,153,133, 5,155,034, and 5,155,035. The spinner flask technique is disclosed in e.g. W. Mueller-Klieser, "*Multicellular Spheroids*", J. Cancer Res. Clin. Oncol., 12: 101-122, 1986. The liquid-overlay technique is disclosed e.g. in J. M. Yuhas et. al., "*A simplified method for production and growth of multicellular tumor spheroids*", Cancer. Res. 37: 3639-3643, 1977. The hanging drop method is disclosed in e.g. Bulletin of Experimental Biology and Medicine, Vol. 91, 3, 1981, Splringer, New York. Most preferred in the present invention is the liquid-overlay technique. Generaly these preparation techniques are all performed under $CO_2$ conditions.

The incubation may be performed at 30° C. to 45° C., preferably at 37° C., in a normoxic atmosphere containing 4 vol.-% to 6 vol.-% $CO_2$, preferably 5 vol.-% $CO_2$ or under hypoxic conditions, i.e. $N_2$ 92%-95%, $O_2$ 5%-8%. The incubation is performed from 5 hours to 9 days, preferably of from 12 hours to 6 days, most preferred of from 24 hours to 96 hours. However, it will be apparent to the skilled artisan that such temperatures and conditions will depend on the source and type of cells used.

The internal environment of a spheroid is dictated by the metabolism and adaptive responses of cells with a well-defined morphological and physiological geometry. Most homotypic spheroids develop concentric layers of heterogeneous cell populations with cells at the periphery and layers of quiescent cells close to a necrotic core. The heterogeneous arrangement of cells in a spheroid mimics initial avascular stages of early tumours.

Thus, suspensions of single cells may be further combined with other cells, for example from established cell lines, primary cells and/or primary or metastatic tissues. Most preferably the tissue is a tumour tissue wherein the cancer cell lines may be cell lines from gastric (e.g. Hs-746T, MKN-28, N87, and the like), colorectal (e.g. HT-29, HCT-116, DLD-1, and the like), liver (e.g. HepG2, and the like), pancreas (e.g. L.6pl, AsPC-1, MiaPACA, and the like), lung (e.g. A549, H358, H1299, and the like), kidney (e.g. 786-O, A-498, CAKI-1, and the like), breast (e.g. MCF-7, BT549, Hs575T, and the like), cervical (e.g. HeLa, and the like), prostate (e.g. PC-3, LNCaP, DU-145, and the like) or glioma (e.g. U251, U373, and the like) cell lines. It will be appreciated that the method is suitable for use with any cell line. In particular preferred are also cell lines from sarcoma or astrocytoma tissue.

Another aspect of the invention is a multicellular spheroid, which is obtained by the process according to the invention.

The process as set forth above leads to spheroids with a nearly homogenous spherical shape, wherein the average diameter of the spheroids reaches from 50 to 2000 µm, preferably from 150 to 1000 µm and most preferred from 200 to 500 µm.

The multicellular spheroids according to the invention can also be characterised in that they exhibit characteristics that substantially mimic those of the tissue of origin, such as: antigen profile and/or genetic profile, tumour biologic characteristics, tumour architecture, cell proliferation rate(s), tumour microenvironments, therapeutic resistance and composition of cell types. Preferably, they exhibit an antigen profile and genetic profile which is substantially identical to that of the tissue of origin.

Thus, the spheroids of the invention exhibit a substantially similar/identical behaviour to that of natural cell systems, e.g. with respect to organization, growth, viability, cell survival, cell death, metabolic and mitochondrial status, oxidative stress and radiation response as well as drug response.

The multicellular spheroids according to the invention can be used for diagnostic and/or therapeutic purposes, for example, pharmacokinetic profiling, pharmacodynamic profiling, efficacy studies, cytotoxicity studies, penetration studies of compounds, therapeutic resistance studies, antibody generation, personalized or tailored therapies, RNA/DNA "drug" testing, small molecule identification and/or testing, biomarker identification, tumour profiling, hyperthermia studies, radioresistance studies, anti-angiogenic studies co-culturing with endothelial cells and the like.

In one aspect, the multicellular spheroids can be obtained from benign or malignant tissues or from primary cells and used for the screening of compounds, for example, as new therapeutic agents or screening for e.g. chemotherapeutic agents wherein the response of the spheroid to the chemotherapeutic agent can be determined. It is thus possible to see whether a chemotherapeutic agent has an effect and/or side effects on the multicellular spheroid, e.g. whether it causes cell death (apoptosis) or other biologic effect.

In the sense of the present invention, preferably the term "chemotherapeutic agent" should be understood as to include all chemical substances used to treat disease. More particularly, it refers to antineoplastic drugs used to treat cancer or the combination of these drugs into a standardized treatment regimen. In its non-oncological use, the term may also refer to antibiotics (antibacterial chemotherapy). Other uses of cytostatic chemotherapy agents are the treatment of autoimmune diseases such as multiple sclerosis and rheumatoid arthritis, viral infections, heart diseases and the suppression of transplant rejections. It will of course be apparent to the skilled artisan that such chemotherapeutic agent need not be limited to substances used to treat disease. Thus, the term may be applied more loosely to refer to any agent that the skilled person wishes to expose the spheroids to determine whether said agent has an effect, for example, on the behaviour or biological characteristics of the spheroids.

By way of non-limiting example, chemotherapeutic agents may include: alkylating agents, antimetabolites, anthracyclines, plant alkaloids, topoisomerase inhibitors, and other anti-tumour agents, antibodies such as monoclonal, single chain or fragments thereof and the new tyrosine kinase inhibitors e.g. imatinib mesylate (Gleevec® or Glivec®), small molecules, tyrosine kinase receptor inhibitors, anticalins, aptamers, peptides, scaffolds, biosimilars, generic drugs, siRNA and RNA or DNA based agents.

In the next process step of the present invention the combination of fibroblasts with the single cell suspension is incubated, preferably in the presence of $CO_2$. The concentration of $CO_2$ is thereby preferably from 1 vol.-% to 10 vol.-%, preferred from 2 vol.-% to 8 vol.-%, more preferred from 4 vol.-% to 6 vol.-% and most preferred 5 vol.-%.

Incubation can also be carried out in the presence of water vapour. Possible preparation techniques are e.g. the liquid-overlay technique, the spinner flask technique, the high aspect rotating vessel (HARV) technique or the hanging drop method. These methods are known to the skilled artisan. The HARV technique is inter alia disclosed in U.S. Pat. Nos. 5,153,131, 5,153,132, 5,153,133, 5,155,034, and 5,155,035. The spinner flask technique is disclosed in e.g. W. Mueller-Klieser, "Multi-cellular Spheroids", J. Cancer Res. Clin. Oncol., 12: 101-122, 1986. The liquid-overlay technique is disclosed e.g. in J. M. Yuhas et. al., "A simplified method for production and growth of multi-cellular tumour spheroids", Cancer. Res. 37: 3639-3643, 1977. The hanging drop method is disclosed in e.g. Bulletin of Experimental Biology and Medicine, Vol. 91, 3, 1981, Springer, New York. Most preferred in the present invention is the liquid-overlay technique. Generally these preparation techniques are all performed under $CO_2$ conditions.

The incubation may be performed at 36° C. to 38° C., preferably at 37° C., in an atmosphere containing about 4 vol.-% to 6 vol.-% $CO_2$, preferably 5 vol.-% $CO_2$. The incubation is performed from 5 hours to 9 days, preferably of from 12 hours to 6 days, most preferred of from 24 hours to 96 hours. However, it will be apparent to the person skilled in the art that such temperatures and conditions will depend on the source and type of cells used.

Another aspect of the invention is a multi-cellular spheroid, which is obtained by the process according to the second aspect of the invention. The spheroid comprises a mixture of fibroblasts with one or more other cell types (heterotype spheroids). In case of heterotype spheroids with tumour cells, the fibroblasts are preferably isolated from the same tissue type and are most preferred fibroblasts from a malignant tissue of the same type. It is, however, also possible to combine the tumour cells with any other type of fibroblast, for example fibroblasts from benign tissue (of the same type).

The process as set forth above leads to spheroids with a nearly homogenous spherical shape, wherein the average diameter of the spheroids reaches from 50 µm to 2000 µm, preferably from 150 µm to 1000 µm and most preferred from 200 µm to 500 µm. Thereby spheroids consisting of fibroblasts only possess a smaller diameter than spheroids comprising different cell types.

The multi-cellular spheroids according to the invention can also be characterised in that they exhibit characteristics that substantially mimic those of the tissue of origin, such as: antigen profile and/or genetic profile, tumour biologic characteristics, tumour architecture, cell proliferation rate(s), tumour microenvironments, therapeutic resistance and composition of cell types. Preferably, they exhibit an antigen profile and genetic profile which is substantially identical to that of the tissue of origin.

Thus, the spheroids of the invention exhibit a substantially similar/identical behaviour to that of natural cell systems, e.g. with respect to organization, growth, viability, cell survival, cell death, metabolic and mitochondrial status, oxidative stress and radiation response as well as drug response and ability to penetrate into the spheroids.

In a further aspect, the present invention also pertains to spheroids which are only made from fibroblasts according to the present invention. In this aspect, it is possible that the fibroblasts are from the same (tissue) origin or form different origins.

The multi-cellular spheroids according to the invention can be used for screening compounds for diagnostic and/or therapeutic purposes, for example, pharmacokinetic profiling, pharmacodynamic profiling, efficacy studies, cytotoxicity studies, therapeutic resistance studies, antibody generation, personalized or tailored therapies, RNA/DNA "drug" testing, small molecule identification and/or testing, biomarker identification, tumour profiling and the like.

In one aspect, the multi-cellular spheroids can be, at least in part, obtained from tumour tissue or from primary cells and used for the screening of compounds, for example, as new therapeutic agents or screening for e.g. chemotherapeutic agents wherein the response of the spheroid to the chemotherapeutic agents can be determined. It is thus possible to see whether a chemotherapeutic agent has an effect on the multicellular spheroid, e.g. whether it causes cell death (apoptosis) or other biologic effect.

EXAMPLES

The present invention will now be more fully described by way of examples that are intended to aid understanding of the invention, but are not intended, and should not be construed, to limit the scope of the invention in any manner.

Example 1

Preparation of Primary Fibroblast Cultures from Mucosa and Tumour Tissue of the Human Stomach Materials:
a) Fibroblast growth medium (=transport medium) comprising: fibroblast culture medium (500 ml DMEM) and 20% FCS (100 ml), 0.1 mg/ml Cefazoline 2.0 μg/ml, 0.250 μg/ml Fungizone.
b) 1% gelatine solution: 5 g gelatine type A in sterile distilled water (500 ml).
c) Trypsin-EDTA solution: Trypsin-EDTA (10 ml) and PBS (without CaC12 and without MgC12) 40 ml.
d) Freezing medium: 9 ml fibroblast culture medium, 9 ml FCS and 2 ml dimethyl sulfoxide (DMSO).
Preparation:
Mucosa and primary tumour are prepared separately. 3 ml fibroblast growth medium was put in a cell culture dish and the mucosa or primary tumour tissue was added. The tissue was reduced to small pieces with the aid of a scalpel. The reduction was finished when tissue suspension was able to be drawn through a 5 mm pipette (for the mucosa tissue) or a 10 mm pipette (for the tumour tissue). The suspension was transferred into a cell culture bottle coated with a 1% gelatine solution and incubated for 24 hours at 37° C. Following the initial incubation the culture was checked for contamination. If contamination was detected the sample was discarded. If there was no evidence of contamination, the culture was incubated for a further 24 hours.

Due to the different morphology of tumour tissue and mucosa tissue, the culture conditions for these two kinds of tissue are slightly different.

The growth medium for the tumour tissue was removed completely and replaced taking care that the tissue pieces remained in the cell culture bottle. Then, 10 ml of fresh fibroblast growth medium was added to the tumour tissue and the tumour tissue re-suspended.

Half of the growth medium of the mucosa tissue was removed and replaced with 5 ml of fresh fibroblast growth medium and the mucosa tissue re-suspended.

The cell culture bottle comprising either the tumour or mucosa tissue then further incubated at 37° C. After 3 to 4 days in culture the growth medium was replaced by fresh growth medium according to the procedure outlined above. The procedure of incubation for 3 days to 4 days followed by exchange of the growth medium was repeated about three times.

Following the third incubation the fibroblast growth medium was discarded completely and replaced with 10 ml of fresh fibroblast culture medium (10 ml).

The tissue was incubated for a further 3 days to 4 days in the fresh fibroblast culture medium during which time pieces of the tissue adhered to the surface of the vessel and fibroblasts grew in the form of cell nests.

The vessel was treated mechanically to detach the adhered tissue from surface of the vessel. The fibroblast cell nests remained attached. The tissue pieces were removed using a pipette and transferred into a second culture vessel coated with a 1% gelatine solution and containing fresh fibroblast culture medium.

The vessel containing the cell nests was washed with 12 ml PBS to remove any remaining tissue fragments.

Fibroblast cell nests were removed from the surface of the vessel by adding 4 ml Trypsin/EDTA solution (2 ml 2X-Trypsin/EDTA+2 ml 1 mmol, EDTA) and incubating at 37° C. for 10 minutes. Following incubation the fibroblast cells were detached from the surface of the vessel by light knocking on the vessel with a hand and washing with 12 ml of fibroblast culture medium. The detached fibroblasts were transferred to a 50 ml flacon tube.

5 ml of fibroblast culture medium was added and the cells were pelleted by centrifugation at 1200 rpm for 8 minutes at 37° C. The supernatant was removed and the cell pellet re-suspended in 10 ml fibroblast culture medium. The re-suspended cell nests grew to confluency during further incubation (for between 2 to 6 times) at 37° C. and were then harvested for further use or storage.

For storage the suspension is centrifuged as above and the resultant supernatant removed. The cell pellet is tapped or lightly vortexed to release the pelleted cells. The cell pellet was then re-suspended in 2 ml of freeze medium and flash frozen in a falcon tube in a −80° C. refrigerator before transfer after 7 days into liquid nitrogen storage.

To the second vessel containing the tissue fragments, 10 ml of fresh culture medium was added and then incubated at 37° C. Further fibroblast cell nests were generated and separated from the tissue as described above. This procedure was repeated about four times, following which the tissue fragments and the suspension were discarded.

Example 2

Re-Cultivation of Primary Fibroblasts

A T75 bottle was prepared by coating with a 1% gelatine solution. Culture medium comprising RPMI 1649 and Glutamax L with 10% FCS was prepared. The frozen fibroblast cells were defrosted and added to the culture medium and incubated as before.

Example 3

Preparation of Heterotypic Spheroids Made of Colon Rectal Cancer

A colorectal cancer tissue biopsy with a size of about 0.5 cm$^3$ was obtained from a patient. The tissue was broken up using mechanical and enzymatic means and the cells were suspended in RPMI 1640 medium containing Glutamax I.

The viability of the cells was tested using the trypan blue exclusion test and the concentration of cells adjusted to $10^6$ cells/ml medium with the aid of a Neubauer counter chamber. The cell suspension was combined with an equal concentration of fibroblasts prepared in Example 1. The aim was to achieve a concentration of $5\times10^4$ cells/100 µl. This is approximately $5\times10^5$ cells/ml or $6\times10^6$ cells in 12 ml.

The final suspension contained 6 ml of cell suspension, 5.5 ml RMPI 1640+Glutamax and 0.6 ml Methocel® (corresponding to ~5%).

For each well plate 12 ml cell suspension was prepared (96 well×100 µl/well=~10 ml+2 ml excess=12 ml) and 100 µl of suspension transferred to each well. The cell suspension was then incubated at 37° C. in the presence of 5% $CO_2$ for 24 hours.

After 24 hours multi-cellular spheroids had formed exhibiting a homogeneous shape with a mean diameter of about 250 µm.

Example 4

Preparation of Heterotypic Spheroids by Combining a Homotypic Cell Line With a Primary Cell Type Homotypic cells from a human gastric carcinoma cell line (Hs746T) were suspended in RPMI 1640 culture medium containing Glutamax I™ or L-Glutamine.

The viability of the cells was tested with the trypan-blue exclusion test and the concentration of cells was adjusted to $10^6$ cells/ml medium with the aid of a Neubauer counter chamber. Cellulose ether was then added to the cell suspension and the suspension transferred to a 96-well plate with the following amounts of reagents:

For each well plate 12 ml cell suspension was prepared (96 well×100 µl/well=~10 ml+2 ml excess=12 ml), to provide a concentration of cells of $5\times10^4$ cells/100 µl medium corresponding to $5\times10^5$/ml corresponding to $6\times10^6$/12 ml.

The final suspension contained 6 ml of the cell suspension, 5.5 ml RMPI 1640+Glutamax™ and 0.6 ml cellulose ether (=5%).

The Hs746T cell suspension was mixed with fibroblasts (in either a 1:1 ratio or 9:1 ratio) and transferred with a multi-channel pipette to a 96-well plate in an amount of 100 µl/well. The cell suspension was then put in an incubator and incubated at 37° C. in the presence of 5% $CO_2$ for 24 hours.

After 24 hours heterotypic multicellular spheroids had formed. The spheroids comprised both cells of the Hs746T cell line and fibroblast cells and exhibited a homogeneous shape with a mean diameter of about 200 µm.

The invention claimed is:

1. A process for the preparation of heterogenic fibroblasts comprising the steps of:
   a) Providing a cell-containing tissue sample;
   b) Preparing a suspension of primary cells comprising tissue pieces from the cell-containing tissue sample in a medium;
   c) Culturing the suspension of primary cells comprising tissue pieces in a vessel coated with a matrix wherein a batch of fibroblast cell nests is generated on the matrix of the vessel;
   d) Separating the fibroblast cell nests of step c) from the suspension of primary cells comprising tissue pieces;
   e) Repeating steps c) to d) at least once whereas the suspension of primary cells comprising tissue pieces of step d) is re-used within step c) to generate at least one more batch of fibroblast cell nests;
   wherein the at least two batches of fibroblast, cell nests obtained through steps c) to e) have different types of fibroblasts, and
   wherein a combination of the at least two batches of fibroblast cell nests provides heterogenic fibroblasts.

2. The process according to claim 1, wherein the suspension of step b) is also treated with an enzymatic composition containing one or more enzymes selected from the group consisting of proteases, metalloendopeptidases, DNases, hyaloronidases, before culturing according to step c).

3. The process according to claim 2, wherein the enzymatic composition also contains a serum-free medium selected from the group consisting of RPMI, DMEM, F15, MEM, BMEEARL, HAMFSF-12, Leibovitz L-15, McCoys 5A, medium 199, Waymouth medium and HANK-solution.

4. The process according to claim 1, wherein the cell-containing tissue sample is a sample from a tissue selected from the group consisting of a benign tissue, malignant tissue or tumor tissue.

5. The process according to claim 1, wherein the medium is a growth medium.

6. The process according to claim 1, wherein the suspension of primary cells comprising tissue pieces is cultured in the medium at 37° C. for at least 3 days in step c).

7. The process according to claim 6, wherein the suspension of primary cells comprising tissue pieces is cultured in a vessel coated with a gelatine solution.

8. The process according to claim 1, wherein the medium comprises DMEM and FCS or FBS.

9. The process according to claim 1, wherein steps c)-d) are repeated at least 3 times.

10. The process according to claim 1, wherein steps c)-d) are repeated at least 5 times.

11. The process of claim 2, wherein the protease is selected from the group consisting of serine protease, trypsin, dispase, and neutral protease.

12. The process of claim 2, wherein the metalloendopeptidase is selected from the group consisting of collagenase and thermolysin.

13. The process of claim 12, wherein the collagenase is selected from the group consisting of interstitial collagenase and neutrophil collagenase.

14. The process of claim 4, wherein the benign tissue is selected from the group consisting of a gastric tissue, colorectal tissue, liver tissue, lung tissue, mucosal tissue, cerebral tissue, pancreas tissue, hepatic tissue, dermal tissue, prostate or periprostatic tissue, gastric tissue, colonic tissue, ovarial tissue, breast tissue, cervical tissue and glioma tissue.

15. The process of claim 4, wherein the malignant tissue is an inflammatory tissue.

16. The process of claim 4, wherein the tumour tissue is a tissue from a metastatic or primary tumour.

17. The process of claim 4, wherein the tumour tissue is a gastric, pancreas, colorectal, liver, lung, breast, cervical, mucosal, cerebral, hepatic, dermal, colonic, ovarial, sarcoma, prostate or glioma tumor.

18. The process according to claim 5, wherein the growth medium comprises a buffer, a serum, an antibiotic and/or a fungicide.

19. The process according to claim 18, wherein the buffer is phosphate buffered saline (PBS), the serum is foetal calf or bovine serum (FCS or FBS), the antibiotic is Cefazoline and the fungicide is amphotericin B.

\* \* \* \* \*